United States Patent [19]

Osterholt et al.

[11] Patent Number: 6,107,496
[45] Date of Patent: Aug. 22, 2000

[54] PROCESS FOR THE PREPARATION OF CYCLIC ESTERS

[75] Inventors: Clemens Osterholt, Dorsten; Josef Metz; Guenther Koehler, both of Marl, all of Germany

[73] Assignee: Huels Aktiengesellschaft, Marl, Germany

[21] Appl. No.: 09/261,132

[22] Filed: Mar. 3, 1999

[30] Foreign Application Priority Data

Mar. 3, 1998 [DE] Germany .......................... 198 08 844

[51] Int. Cl.[7] ...................... C07D 323/04; C07D 407/00
[52] U.S. Cl. .............................................. 549/274
[58] Field of Search ................................. 549/274

[56] References Cited

U.S. PATENT DOCUMENTS

| | | | |
|---|---|---|---|
| 4,803,288 | 2/1989 | Kitamura et al. | 549/267 |
| 5,717,111 | 2/1998 | Koehler et al. | 549/266 |

*Primary Examiner*—John Kight
*Assistant Examiner*—Raymond Covington
*Attorney, Agent, or Firm*—Oblon, Spivak, McClelland, Maier & Neustadt, P.C.

[57] ABSTRACT

A process for the preparation of cyclic esters of the general formula:

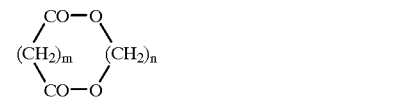

formula I in which m is an integer from 6–14 and n is an integer from 2–6, which comprises heating a dicarboxylic acid bis (glycol) ester of the general formula:

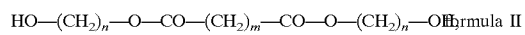

in which m and n are as defined above, (b) optionally, up to 100% by weight, based on the weight of ester II, of esters of the general formula:

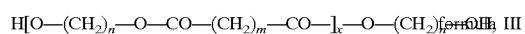

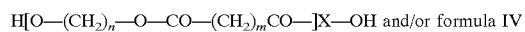

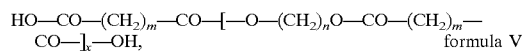

in which m and n are as defined previously and x is an integer >1, and (c) a glycol of the general formula:

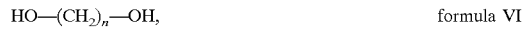

formula VI in which n has the same numerical value as in formula I–V, (d) an inert high-boiling reaction medium, and (e) a catalyst.

20 Claims, No Drawings

PROCESS FOR THE PREPARATION OF CYCLIC ESTERS

BACKGROUND OF THE INVENTION

FIELD OF THE INVENTION

The invention relates to a process for the preparation of cyclic esters, preferably 12- to 20-membered, of the general formula:

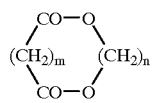

formula I in which m is an integer from about 6–14 and n is an integer from about 2–12, by cyclization of dicarboxylic acid bis (glycol) esters or dicarboxylic acid bis(hydroxyalkyl) esters of the general formula:

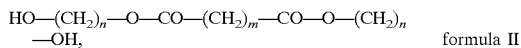

formula II in which m and n are as defined above.

DISCUSSION OF THE BACKGROUND

Cyclic esters of this type and in particular the cyclic ethylene brassylate formed from brassylic acid and ethylene glycol, are extremely important in the perfume industry as a constituent of perfumes having an ambergris or musk note and depolymerization of oligomeric or polymeric glycol esters of corresponding carboxylic acids. The depolymerization is normally carried out at high temperatures and under reduced pressure in such a way that the resulting products can be distilled off and obtained by condensation. The cyclizing depolymerization is described, for example, in J. Am. Chem. Soc. 57 (1935), 929–34 and U.S. Pat. No. 4,175,321.

It is disclosed in U.S. Pat. No. 4,709,058, JP 55-120581 and DE 32 25 341, that the preparation of cyclic esters by cyclizing depolymerization is advantageously carried out using inert high-boiling reaction media. A significant problem with any cyclizing depolymerization is that, under the reaction conditions, relatively high molecular weight esters may form through polycondensation of oligomers or polymers having terminal carboxyl groups with other oligomers or polymers which carry terminal hydroxyl groups, with the elimination of water, or through polycondensation of oligomers or polymers having terminal hydroxyalkyl groups with the elimination of glycol. The desired intramolecular formation of cyclic monomeric products is thus accompanied by an undesired intermolecular formation of linear, unreactive highly polymeric esters. This not only reduces the yield of desired products, but also causes process engineering problems.

In the processes described hitherto, the reaction is generally carried out batchwise or semicontinuously. For a synthesis on a small scale, for example on a laboratory or pilot-plant scale, problems are relatively minor. When the process is applied on an industrial scale, however, there are considerable disadvantages when conducting the reaction batchwise or continuously in a stirred reactor. Relatively high molecular weight products are formed which lower the thermal conductivity of the reaction mixture while simultaneously increasing the viscosity thereof. This hinders the recovery of the desired monomeric products by distillation, and favors the formation of undesired high molecular weight products. As the amount of the undesirable products increases, this results in an increase in the amount of bottom products formed, and these must be disposed of. If the reaction is not terminated at the proper time, it is possible that the contents of the reactor may solidify.

Moreover, it is not technically efficient to provide the amount of energy required for the cyclizing depolymerization in a stirred reactor and at the same time provide as large an evaporation surface as possible for the recovery of the cyclic ester product and the glycol which has formed as well as any glycol additionally introduced, and glycol which has unavoidably distilled off with the ester product.

According to European Patent Application No. 929 07 653.7, this problem can be solved by using a special, horizontal thin-film evaporator. However, it must be operated at very high temperatures of >300° C. and with virtually neat polymeric feed, and serious problems may arise due to the formation of high polymeric products.

SUMMARY OF THE INVENTION

It is an object of the invention to provide a process for preparing cyclic esters with minimum formation of undesirable high molecular weight by products.

It is another object of the invention to provide a process for the formation of cyclic esters which can be conducted on an industrial scale in a stirred reactor under batchwise or continuous conditions.

The above problems are solved and the objects of the invention achieved by the present process which can be conducted in a manner which is easy to carry out industrially. The invention provides for the preparation of cyclic esters, preferably containing about 12–20 ring members, of the general formula:

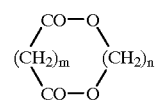

formula I in which m is an integer from about 6–14 and n is an integer from about 2–12, by cyclization of dicarboxylic acid bis (glycol) esters of the general formula:

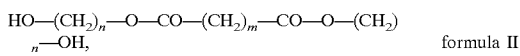

formula II in which m and n are as defined above. The process comprises heating (a) a dicarboxylic acid bis(glycol) ester of formula II, (b) optionally, up to 100% by weight, based on the ester of formula II, of esters of the general formula:

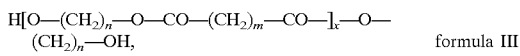

formula III

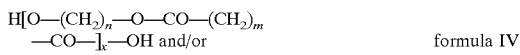

formula IV

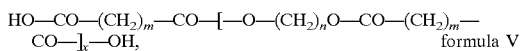

formula V in which m and n have the same numerical value as in formula I and II and x is an integer >1, preferably from 2–10, (c) a glycol of the general formula:

formula VI in which n has the same numerical value as in formula I–V, in molar amounts of from about 1 to about 50 times, preferably from about 2 to about 20 times the molar amounts of ester II and the dicarboxylic acid units of esters III–V, and (d) an inert high-boiling reaction medium in amounts of from about 0.1 to about 20 times, preferably from about 1 to about 15 times and, in particular, from about 2 to about 10 times the amount by weight of the total of esters II–V, in the presence of (e) a catalyst.

The reaction is conducted at temperatures of from about 150 to about 350° C., preferably from about 180 to about 300° C. and, most preferably, from about 200 to about 280° C., at a reduced pressure of from about 0.1 to about 500 mbar, and preferably from about 0.5 to about 100 mbar, in an evaporator having a large surface area. As a result, the cyclic ester I is produced with the elimination of glycol and is distilled off together with glycol VI and isolated by condensation.

Surprisingly, the present process produces yields of cyclic esters of >90% of theory, despite the presence of excess glycol VI which would be expected to shift the transesterification equilibrium in the direction of the dicarboxylic acid bis(glycol) esters II, i.e. suppress the cyclization reaction.

DETAILED DESCRIPTION OF THE PREFERRED EMBODIMENTS

The present process is advantageously carried out continuously with recycling of the inert high-boiling medium, which contains the catalyst and unreacted esters II–V. Preferably, the continuous process is carried out in such a way that the solution of dicarboxylic acid bis(glycol) ester II in the corresponding glycol, which solution contains the catalyst and optionally esters III–V, is introduced into the recycled inert high-boiling medium, and the resulting mixture is introduced into the evaporation zone, which is also the reaction zone. The cyclic ester I and glycol VI are removed from this mixture by distillation. The starting materials, i.e. the esters II–V, are largely reacted in only one pass. Thus, in an optimum procedure, generally only 1–10% of the starting materials, based on the inert high-boiling medium, remain unevaporated and, following enrichment with fresh starting material and glycol, are recycled to the evaporation zone. The residence time in the large surface area evaporator is advantageously from about 0.5 to about 10 minutes per pass. The time is controlled by a pump which generates the cycle. After steady state has been achieved, up to 100% of the starting materials are converted into the cyclic ester I. Over the course of an extended production cycle, which involves a start-up phase and steady state, well over 95% of the starting materials, depending on the length of the cycle, are converted into the desired ester I.

The esters II–V are derived from dicarboxylic acids and glycols (or diols). Suitable dicarboxylic acids have, for example, from 2–20, preferably from 4–12, carbon atoms between the carboxyl groups. Examples thereof are, inter alia, succinic acid, adipic acid, suberic acid, sebacic acid (1,10-decanedioic acid), 1,12-dodecanedioic acid and brassylic acid (1,13-tridecanedioic acid). Suitable diols include those having from about 2 to about 12 carbon atoms between the hydroxyl groups. The following diols may be mentioned: ethylene glycol, ethylene diglycol, 1,3-propanediol, 1,4-butanediol, 1,6-hexanediol, 1,8-octanediol and 1,12-dodecanediol.

A glycolic solution of esters II–V suitable for carrying out the process of the invention can be prepared using customary esterification or transesterification catalysts by direct esterification of the dicarboxylic acid with the glycol VI, or by transesterification of a dicarboxylic acid dialkyl ester of an aliphatic, low molecular weight alcohol of about 1 to about 6 carbon atoms, and glycol VI with elimination of the aliphatic low molecular weight alcohol, or by depolymerization of a highly polymeric ester of the formula III–V, in which x is, for example,=>10, with excess glycol VI. In the latter case, the highly polymeric esters (x=>10) are depolymerized to give a mixture of monomeric esters II and relatively high molecular weight esters III (x=2–10). The formation of relatively high molecular weight esters IV and V having free carboxyl groups is not favored because of the glycol used. In all cases, the formation of the dicarboxylic acid bis(glycol) ester II increases with increasing amounts of glycol VI. Glycolic solutions of ester II which contain virtually no esters III can only be prepared with very large molar excesses of glycol VI, for example, more than 200 mol per mole of dicarboxylic acid. In practice, ester II and ester III will always be present. For example, solutions of esters II–V in which ester II is present in amounts of from 70–95% by weight, based on the total amounts of esters II–V, can be used successfully. Such solutions are produced if from 5–20 mol of diglycol are used per mole of dicarboxylic acid unit in esters II–V.

If the glycolic solutions of esters II–V are prepared in the manner described above, they usually contain the required amounts of glycol VI. If this is not the case or if the amount is to be increased for optimization, further glycol can be added. Optimization can still be achieved even if, in the interest of high space-time yield, less glycol has been added than is desirable for the cyclization reaction. Preferably, the glycol is present in a molar amount of from about 2 to about 20 times the molar amount of the esters II–V, based on the dicarboxylic acid units of the esters.

Catalysts which may be used both for the preparation of the glycolic solutions of the esters II–V and also for the cyclization reaction are the customary acidic or basic esterification catalysts, which are also known as transesterification catalysts. Examples of suitable catalysts are acids which are sufficiently stable under the process conditions, such as sulfuric acid, sodium hydrogen sulfate, are acids which are sufficiently stable under the process conditions, such as sulfuric acid, sodium hydrogen sulfate, phosphoric acid and sulfonic acids; also alkali metal and alkali metal alkoxides; and compounds of magnesium, manganese, cadmium, iron, cobalt, tin, lead, aluminum and titanium. Preference is given to homogeneously dissolved catalysts of the Lewis acid type. These would include compounds which are proton donors. The iron(III) complexes described in German Patent Application (O.Z. 5276), the entire disclosure of which is incorporated herein by reference, can also be used as catalysts in the present invention.

The catalysts used for the preparation of the glycolic solutions of the starting materials II and III can remain in the solution, since they can also be used as catalysts for the cyclization reaction. This applies in particular when the catalysts are dissolved homogeneously. Alternatively or in addition to the above, catalyst may be introduced with the inert high-boiling reaction medium. If the process of the invention is carried out continuously, further catalyst can be added to the recycled inert high-boiling medium, which already contains catalyst.

Preferably, from about 0.01 to about 10% by weight of catalyst is present in the evaporation zone per mol of dicarboxylic acid bis(glycol) esters II or dicarboxylic acid units in the esters III–V. If the process is carried out continuously, the desired catalyst concentration in the evaporation zone can be controlled by controlling the circulation rate of the inert high-boiling medium. At a high circulation rate, high concentrations of catalyst can be provided in the evaporation zone without having to recycle correspondingly large amounts of catalyst with the glycolic solution of the starting materials II and III–V. This is one advantage of the continuous variant of the novel process.

Suitable inert high-boiling media, i.e. those boiling above >400° C. at atmospheric pressure, include polyalkylene glycol dialkyl ethers. The following specific examples may be mentioned: polyethylene glycol dimethyl ether (PEG DME) 1000, 2000 or 5000; polyethylene glycol diethyl ether (PEG DEE) 1000, 2000, 5000; similar polypropylene glycol dimethyl or diethyl ethers and the dimethyl or diethyl ethers of mixed polyethylene/propylene glycols having a block structure or random distribution can be used. The numbers above refer to the molecular weights.

In addition to specific molar amounts of glycol, based on the ester II and the dicarboxylic acid units in the esters III–V, the amount by weight of inert high-boiling medium, based on the total amounts by weight of the esters II and III–V, is also a unique feature of the invention. The result of these measures is that extensive conversion of esters II–V to cyclic ester I can be achieved in just one pass, so that in a continuous operation of the process, there is virtually no accumulation of nonvolatile, higher molecular weight polymeric products in the recycled reaction medium. The desired amount of inert, high-boiling medium is determined by the amount of esters II–V and glycol VI added per unit of time, and by the optimum residence time in the evaporation zone. This in turn, depends, inter alia, on the equipment, in particular the type of evaporator and the recirculating performance of the pump, and also on the temperature in the evaporation zone. In each case, the relevant parameters must be matched to one another in such a way that from about 0.1 to about 20 times, preferably from about 1 to about 15 times and most preferably from about 2 to about 10 times, the amount of insert high-boiling medium by weight, based on the total amounts by weight of the esters II–V must be present in the evaporation zone. A greater degree of dilution, i.e. a 20-fold plus amount of inert high-boiling medium, offers no economic advantage, but neither is it a disadvantage for the progress of the reaction.

Suitable evaporators, which function as reactors in the present process include any conventional evaporators having a large surface area, such as thin-film, falling-film, trickle-film and short-path evaporators. In these cases, the required amount of heat can advantageously be introduced directly via the evaporator. If a recycle stream of the inert high-boiling medium is passed over a heat exchanger, then the reaction can also be carried out in a trickle bed reactor. Another suitable variant is a stirred reactor having a fixed-bed catalyst, which is connected to an evaporator having a large surface area via a circuit. Also suitable is a technique where the preheated high-boiling reaction medium containing starting material II–V, glycol VI and catalyst can be sprayed into an evaporator in which a heated inert carrier gas flows and carries out the ester I and excess glycol VI, while the high-boiling reaction medium flows from the evaporator as a liquid. In suitable evaporators, the high-boiling reaction medium, which contains starting material II–V, glycol VI, catalyst and, after the reaction has progressed, also cyclic ester I, is present as a thin film less than about 2 cm in thickness, advantageously less than about 0.5 cm in thickness, or in drop form, and thus offers a large, evaporation-promoting specific surface area. The residence times of the high-boiling reaction medium during which the conversion from the starting material to the product is completed are correspondingly short. Large-surface-area evaporators thus permit, at reaction temperatures suitable for the respective cyclic ester, at least 80%, and advantageously at least 90%, conversion of the starting material within a residence time of less than 5 minutes, advantageously less than 2 minutes. In most cases the residence times are in the seconds range. In all cases, the distillate separates into two phases, the cyclic ester I being the upper phase and the glycol VI the lower phase.

It is an important function of the invention to employ the glycol VI in a molar excess and to use an evaporator having a large surface area. Although the glycol has the lowest boiling point of all the components in the reaction and is quickly removed from the reaction mixture, it is surprising that this has no adverse impact on the efficiency and yield of the process.

Further, the present process leads to high, almost quantitative yields of cyclic ester even when, in addition to the ester II, higher molecular weight esters III–V are present in considerable amounts. Should high polymeric esters accumulate in the recycled inert high-boiling medium, these can be converted into cyclic ester I by temporarily increasing the amount of glycol added. Alternatively, it is also possible to use some of the inert high-boiling medium enriched with higher molecular weight esters in the preparation of the glycolic solution of the esters II and III. Degradation to esters II and III–V also takes place here.

The present invention is illustrated in greater detail by the following examples which are not intended to be limiting of the claims unless otherwise specified.

EXAMPLES 1–6

General procedure

X kg/h of dicarboxylic acid bisglycol ester of the general formula II where m=11 and n=2 (bishydroxyethyl brassylate), containing 0.12% by weight of the monosodium salt of the Fe(III) ethylenediaminetetraacetic acid complex, and Y kg/h of ethylene glycol are fed to a reactor which contains polyethylene glycol (2000) dimethyl ether as high-boiling medium. The reactor consists of a heated thin-film evaporator having a surface area of about 1.5 m$^2$ and a still having a volume of 50 l incorporated into the heating cycle and a return line to the top of the falling-film evaporator, which is provided with a heat exchanger on the inlet side. The thin-film evaporator is operated at a pressure p. The temperature of the stream entering the evaporator is $T_{max}$, and the temperature of the stream leaving the evaporator is $T_y$. The rotor of the thin-film evaporator is operated at rotational speed U.

The vapors from the thin-film evaporator are passed through a vapor pipe to a condenser. The condensate passes into a receiver connected downstream of a separation vessel. The upper phase drawn off from the separation vessel is ethylene brassylate containing about 7% by weight of ethylene glycol. Simple distillation thereof produces pure ethylene brassylate. The lower phase consists of ethylene glycol containing traces of ethylene brassylate. It is recycled into the process together with fresh ethylene glycol.

The feed amounts, process conditions and results of the examples are given in the table below.

TABLE

| Ex. | X (kg/h) | Y (kg/h) | p (hpa) | $T_v$ (° C.) | $T_{max}$ (° C.) | U (min$^{-1}$) | Yield (kg/h) | Yield (%) |
|---|---|---|---|---|---|---|---|---|
| 1 | 5 | 15 | 0.1 | 280 | 290 | 200 | 4.8 | 96 |
| 2 | 7 | 14 | 0.05 | 240 | 300 | 250 | 6.6 | 94 |
| 3 | 9 | 35 | 25 | 260 | 270 | 300 | 8.7 | 97 |
| 4 | 12 | 28 | 15 | 290 | 300 | 300 | 11.2 | 93 |
| 5 | 9 | 25 | 10 | 300 | 300 | 200 | 8.5 | 94 |
| 6 | 3 | 6 | 75 | 290 | 290 | 300 | 2.7 | 92 |

This application is based on German Patent Application 98 088 44.2, filed Mar. 3, 1998, the entire disclosure of which is incorporated herein by reference.

What is claimed as new and is intended to be secured by Letters Patent is:

1. A process for the preparation of cyclic esters of the general formula:

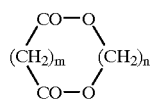
formula I in which m is an integer from about 6 to about 14 and n is an integer from about 2 to about 6, which comprises reacting:

(a) a dicarboxylic acid bis(glycol) ester of the general formula:

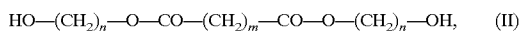
$HO-(CH_2)_n-O-CO-(CH_2)_m-CO-O-(CH_2)_n-OH$, (II)

in which m and n are as defined above, (b) optionally, up to 100% by weight, based on that of the ester II, of at least one ester of the general formula:

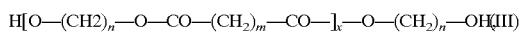
$H[O-(CH_2)_n-O-CO-(CH_2)_m-CO-]_x-O-(CH_2)_n-OH$ (III)

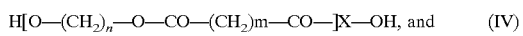
$H[O-(CH_2)_n-O-CO-(CH_2)_m-CO-]X-OH$, and (IV)

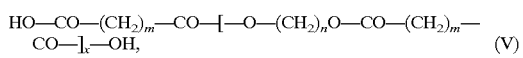
$HO-CO-(CH_2)_m-CO-[-O-(CH_2)_nO-CO-(CH_2)_m-CO-]_x-OH$, (V)

in which m and n are as defined previously and x is an integer >1, (c) a glycol of the general formula:

$HO-(CH_2)_n-OH$, (VI)

in which n has the same numerical value as in formula I–V, present in a molar amount of from about 1 to about 50 times the total molar amounts of ester II and dicarboxylic acid units of esters III–V, and (d) an inert high-boiling reaction medium present in an amount of from about 0.1 to about 20 times the total weight of esters II–V, in the presence of (e) a catalyst.

2. The process as in claim 1 wherein the reaction is conducted at a temperature of from about 150 to about 350° C., at a reduced pressure of from about 0.1 to about 500 mbar, and in an evaporator having a relatively large surface area, whereby the cyclic ester I produced with the elimination of glycol is distilled off together with glycol VI and isolated by condensation.

3. The process as in claim 1, which is conducted continuously with recycling of the inert high-boiling reaction medium, which contains catalyst and unreacted esters II and III, and wherein additional amounts of ester II, optionally esters III–V and glycol VI are added to the mixture being recycled.

4. The process as in claim 1, wherein the glycol is used in molar amounts of from about 2 to about 20 times the total molar amount of ester II and the dicarboxylic acid units in esters III–V.

5. The process as in claim 1, wherein the temperature is from about 180 to about 300° C.

6. The process as in claim 1, wherein the temperature is from about 200 to about 280° C.

7. The process as in claim 2, wherein the pressure is from about 0.5 to about 100 mbar.

8. The process as in claim 1, wherein the inert high boiling reaction medium comprises at least one solvent from the group consisting of higher glycol dialkyl ethers and polyalkylene glycol dialkyl ethers.

9. The process as in claim 1, wherein the inert high boiling reaction medium is present in an amount ranging from about 1 to about 15 times the total amount by weight of esters II–V.

10. The process as in claim 1, wherein the inert high boiling reaction medium is present in an amount ranging from about 2 to about 10 times the total amount by weight of esters II–V.

11. The process as in claim 1, wherein the esters II–V and the glycol VI are used in the form of a glycolic solution selected from the group consisting of that produced by directly esterifying the dicarboxylic acid with excess glycol, that produced by transesterifying a dicarboxylic dialkyl ester having alkyl radicals containing from 1–6 carbon atoms with excess glycol and that produced by depolymerizing polymeric esters of the formula III–V, where x=>10 with excess glycol.

12. The process as in claim 1, wherein the catalyst used is an acidic or basic esterification or transesterification catalyst.

13. The process as in claim 12, wherein the catalyst is sulfuric acid, phosphoric acid, a sulfonic acid, an alkali metal or an alkali metal alkoxide.

14. The process as in claim 12, where the catalyst is a homogeneously dissolved compound of the Lewis acid type.

15. The process as in claim 12, wherein the catalyst is at least one compound of a metal selected from the group consisting of magnesium, manganese, cadmium, iron, cobalt, tin, lead, aluminum and titanium.

16. The process as in claim 11, wherein a catalyst is used to prepare the glycolic solution and the same catalyst is used as catalyst (e).

17. The process as in claim 3, which comprises adding additional catalyst to the recycled inert high-boiling reaction medium.

18. The process as in claim 2, wherein the said evaporator having a large surface area is a thin-film, falling-film or short-path evaporator.

19. The process as in claim 2, wherein the said evaporator having a large surface area is the trickle bed of a column.

20. The process as in claim 1, wherein m=11 and n=2 in formulas I and II.

* * * * *